United States Patent
Ohishi et al.

(10) Patent No.: US 9,161,691 B2
(45) Date of Patent: Oct. 20, 2015

(54) SCANNING OPHTHALMIC IMAGING APPARATUS

(75) Inventors: Masahiro Ohishi, Tokyo (JP); Hitoshi Shimizu, Tokyo (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 70 days.

(21) Appl. No.: 13/989,860

(22) PCT Filed: Sep. 14, 2011

(86) PCT No.: PCT/JP2011/005170
§ 371 (c)(1),
(2), (4) Date: May 28, 2013

(87) PCT Pub. No.: WO2012/093427
PCT Pub. Date: Jul. 12, 2012

(65) Prior Publication Data
US 2013/0242261 A1 Sep. 19, 2013

(30) Foreign Application Priority Data
Jan. 7, 2011 (JP) .................................. 2011-001792

(51) Int. Cl.
*A61B 3/14* (2006.01)
*A61B 3/02* (2006.01)
(Continued)

(52) U.S. Cl.
CPC ............. *A61B 3/1233* (2013.01); *A61B 3/0025* (2013.01);
(Continued)

(58) Field of Classification Search
CPC ................... A61B 3/1025; A61B 2017/00694; A61B 3/1225; A61B 3/113; A61F 2009/00846; A61F 2009/00863; A61F 9/008; A61F 9/00821; A61F 2009/0088; A61F 2009/00848; A61F 2009/00897
USPC ......... 351/200, 205, 206, 209, 221–224, 245, 351/243; 382/128, 131
See application file for complete search history.

(56) References Cited

U.S. PATENT DOCUMENTS 7,789,511 B2 * 9/2010 Aoki et al. .................... 351/205
2008/0225226 A1 9/2008 Fujishiro et al.

FOREIGN PATENT DOCUMENTS

| JP | 09-253052 A | 9/1997 |
| JP | 2008-228781 A | 10/2008 |

(Continued)

OTHER PUBLICATIONS

International Search Report for JP/2011/005170 dated Oct. 18, 2011.

*Primary Examiner* — Joseph P Martinez
*Assistant Examiner* — Brandi Thomas
(74) *Attorney, Agent, or Firm* — Pearne & Gordon LLP

(57) ABSTRACT

Provided is a scanning laser ophthalmoscope capable of accurately superposing multiple photographed images. The scanning laser ophthalmoscope comprises an image generating unit that generates first images based on the light reflected from first laser light and second images based on the light reflected from second laser light. An associating unit associates the first images and the second images based on the first laser light and the second laser light parallelly scanned by the scanning unit. A displacement calculating unit calculates displacements between images regarding multiple first images. The position matching unit matches the positions of multiple second images based on the processing results from the associating unit and the displacements. The superposing unit superposes the multiple second images that have undergone the position matching. The display unit displays an image obtained by superposing the multiple second images.

22 Claims, 10 Drawing Sheets

(51) Int. Cl.
 *A61B 3/12* (2006.01)
 *A61B 3/00* (2006.01)
 *A61B 3/10* (2006.01)

(52) U.S. Cl.
 CPC ................. *A61B 3/10* (2013.01); *A61B 3/1225* (2013.01)

(56) References Cited

FOREIGN PATENT DOCUMENTS

| | | | | |
|---|---|---|---|---|
| JP | 2010-259606 | * | 5/2009 | ............... A61B 3/14 |
| JP | 2010-259606 A | | 11/2010 | |
| WO | 2009045286 A1 | | 4/2009 | |

\* cited by examiner

SCANNING OPHTHALMIC IMAGING APPARATUS

TECHNICAL FIELD

The present invention relates to a scanning ophthalmic imaging apparatus that obtains an image of an eye by scanning light with respect to the eye.

BACKGROUND OF THE INVENTION

Conventionally, a scanning laser ophthalmoscope (hereinafter, may be referred to as "SLO") is known that two-dimensionally scans laser light with respect to a fundus and receives the reflected light therefrom, thereby obtaining a fundus image.

The SLO is capable of photographing using a variety of laser light. For example, blood vessels deep in the fundus, etc. may be photographed by photographing using infrared light as laser light. Alternatively, the state of blood vessels running over the fundus, etc. may be photographed by photographing using excitation light as laser light.

It should be noted that regarding fluorescent photographing, there are cases in which fluorescence based on agents such as fluorescein and indocyanine green is photographed as well as cases in which fluorescence based on particular objects present inside the fundus (autofluorescence) is photographed.

PRIOR ART DOCUMENTS

Patent Document

[Patent Document 1] Japanese Unexamined Published Application 2008-228781

SUMMARY OF THE INVENTION

Problem to be Solved by the Invention

In fluorescent photographing using SLO, there are cases in which, in order to understand the state of blood vessels running over the fundus, a fluorescent agent is intravenously injected into a subject, the state of this fluorescent agent spreading in the fundus is continuously photographed, and the photographed fluorescent images are superposed and displayed on a monitor, etc. Because the fluorescence is weak at this time, it is usual to superpose and display multiple fluorescent images.

In this manner, when assessing the state of blood vessels running over the fundus, photographing is carried out under pitch-dark conditions until the fluorescent agent spreads over the fundus. Moreover, photographing under dim conditions is carried out at an early stage when the fluorescent agent is starting to spread.

Here, an eye is generally not fixed due to the effect of eye movements such as involuntary eye movement, etc. and pulsations. Thus, some kind of standard is necessary in order to superpose images obtained by photographing the eye multiple times without misregistration.

However, as mentioned above, because photographing is commenced from a pitch-dark condition when conducting fluorescent photographing, etc., there is no standard for superposing images photographed at an early stage of photographing. Accordingly, there is a problem in that accurate superposition of multiple fluorescent images is difficult.

The present invention is developed in order to solve the abovementioned problem, with the purpose of providing a scanning ophthalmic imaging apparatus capable of accurately superposing multiple photographed images.

Means for Solving the Problem

In order to achieve the abovementioned purpose, a scanning ophthalmic imaging apparatus according to the present invention has a light source unit that emits first light and second light with a different wavelength from that of the first light. A scanning unit two-dimensionally scans the first light and second light, respectively, at an eye. A light receiving unit respectively receives reflected light of the first light and the second light irradiated onto the eye by the scanning unit. An image generating unit generates a first image based on the reflected light of the first light and a second image based on the reflected light of the second light. An associating unit associates the first image and the second image based on the first light and the second light parallelly scanned by the scanning unit. A displacement calculating unit calculates displacements between a plurality of first images. A position matching unit matches the positions of a plurality of second images based on the processing result from the associating unit and the displacements. A superposing unit superposes the second images that have undergone the position matching. A display unit displays an image obtained by superposing the second images.

Effect of the Invention

The scanning ophthalmic imaging apparatus according to the present invention carries out processing of associating first image and second image based on parallelly scanned first light and second light. Moreover, this scanning ophthalmic imaging apparatus matches the positions of the second images based on the displacements calculated between the first images and the processing result by the associating unit. Moreover, this scanning ophthalmic imaging apparatus matches the positions of the second images based on the processing results from the position matching unit and associating unit. Further, this scanning ophthalmic imaging apparatus displays on the display an image obtained by superposing the second images that have undergone the position matching. According to such a scanning ophthalmic imaging apparatus, the second images may be accurately superposed even when there is no standard for superposition.

DETAILED DESCRIPTION OF THE INVENTION

Configuration of the Optical System

Figure 1:
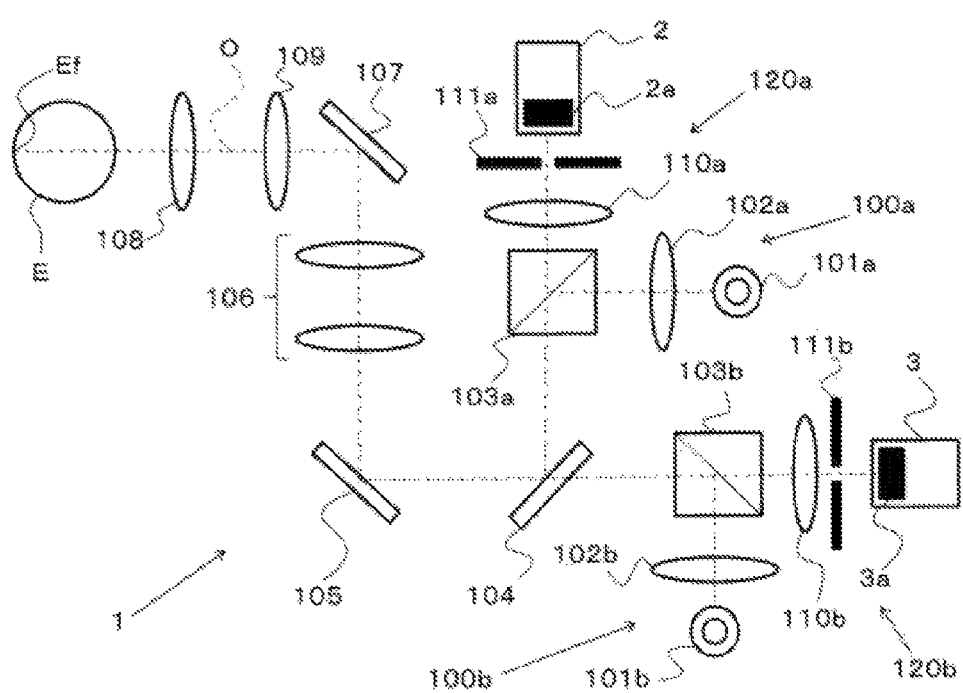
FIG. 1 is a diagram illustrating an optical system of a scanning laser ophthalmoscope according to an embodiment.

First, the configuration of the optical system of the scanning laser ophthalmoscope 1, which is common to each embodiment, is described with reference to FIG. 1.

The optical system of the scanning laser ophthalmoscope 1 comprises two illumination optical systems 100a and 100b, as well as two photographic optical systems 120a and 120b. The illumination optical systems 100a and 100b respectively irradiate laser light of different wavelengths onto the fundus Ef of the eye E. The photographic optical systems 120a and 120b guide fundus reflected light of the laser light to photographing devices 2 and 3, respectively. Further, the dashed-dotted line in FIG. 1 illustrates an optical axis O.

Illumination Optical System

The illumination optical system 100a comprises a laser light source 101a, a collimator lens 102a, a polarization beam splitter 103a, a half-mirror 104, a first scanner 105, a relay lens system 106, a second scanner 107, an objective lens 108, and a focus lens 109.

Moreover, the illumination optical system 100b comprises a laser light source 101b, a collimator lens 102b, a polarization beam splitter 103b, the half-mirror 104, the first scanner 105, the relay lens system 106, the second scanner 107, the objective lens 108, and the focus lens 109.

It should be noted that, in the present embodiment, the half-mirror 104, the first scanner 105, the relay lens system 106, the second scanner 107, the objective lens 108, and the focus lens 109 are common to both illumination optical systems 100a and 100b. In addition, in the present embodiment, the laser light source 101a and laser light source 101b function as the "light source unit."

The laser light source 101a emits first laser light for photographing the fundus Ef. Moreover, the laser light source 101b emits second laser light for photographing the fundus Ef. The laser light sources 101a and 101b comprise, for example, a semiconductor laser, a He—Ne laser, or an Ar laser. The laser light source 101a and laser light source 101b are capable of emitting laser light at different wavelengths. In the present embodiment, the laser light source 101a emits infrared light as the first laser light while the laser light source 101b emits excitation light as the second laser light. In the present embodiment, pulsed first laser light and pulsed second laser light are alternately emitted. Further, by "alternate," the first laser light and the second laser light should be repeatedly emitted a predetermined number of times. That is, for example, a repetition of emitting the first laser light once, emitting the second laser light twice, emitting the first laser light once again, and so on is included as an "alternate" of the present embodiment.

The collimator lens 102a collimates the laser light emitted from the laser light source 101a. The collimator lens 102b collimates the laser light emitted from the laser light source 101b.

The polarization beam splitter 103a reflects only light having a particular polarization component from among the laser light collimated by the collimator lens 102a, and guides this to the half-mirror 104. Moreover, the polarization beam splitter 103b reflects only light having a particular polarization component from among the laser light collimated by the collimator lens 102b, and guides this to the half-mirror 104. Subsequently, the half-mirror 104 guides the laser light reflected by the polarization beam splitters 103a and 103b to the first scanner 105.

The first scanner 105 and the second scanner 107 two-dimensionally scan the laser light guided from the half-mirror 104 with respect to the fundus Ef via the objective lens 108. Specifically, the directions of the reflecting surfaces of the first scanner 105 and the second scanner 107 can be changed in directions orthogonal to each other. A control unit 210 (mentioned later) independently controls the first scanner 105 and the second scanner 107 and changes the direction of the reflecting surface of each scanner, thereby making it possible to carry out two-dimensional scanning of the fundus Ef. In the present embodiment, the first scanner 105 and the second scanner 107 function as the "scanning unit."

For example, a galvano mirror or a polygon mirror is used for the first scanner 105 and the second scanner 107. Moreover, in order to carry out scanning at a faster pace, a resonant scanner may be used. Further, the relay lens system 106 is arranged between the first scanner 105 and the second scanner 107.

Photographic Optical System

Next, the photographic optical systems 120a and 120b are described.

The photographic optical system 120a comprises the objective lens 108, the focus lens 109, the second scanner 107, the relay lens system 106, the first scanner 105, the half-mirror 104, the polarization beam splitter 103a, a condenser lens 110a, a confocal diaphragm 111a, and the photographing device 2.

The photographic optical system 120b comprises the objective lens 108, the focus lens 109, the second scanner 107, the relay lens system 106, the first scanner 105, the half-mirror 104, the polarization beam splitter 103b, a condenser lens 110b, a confocal diaphragm 111b, and the photographing device 3.

Further, in the present embodiment, the half-mirror 104, the first scanner 105, the relay lens system 106, the second scanner 107, and the objective lens 108 are common to the illumination optical systems 100a and 100b.

The focus lens 109 is used for focus adjustment in accordance with a diopter scale of the eye E.

The reflected light of the light irradiated onto the fundus Ef by the illumination optical systems 100a and 100b passes the objective lens 108 and focus lens 109, is reflected by the second scanner 107, passes the relay lens system 106, and is reflected by the first scanner 105, then guided to the half-mirror 104. Further, the "(fundus) reflected light" of the present embodiment includes "fluorescence," which is generated by the excitation light.

In the photographic optical system 120a, the half-mirror 104 reflects the reflected light based on the light irradiated by the illumination optical system 100a towards the polarization beam splitter 103a. Moreover, the reflected light based on the light irradiated by the illumination optical system 100b transmits through the half-mirror 104 and is guided towards the polarization beam splitter 103b.

Only light with a particular polarization component from among light from the half-mirror 104 (reflected light of the fundus Ef) transmits the polarization beam splitters 103a and 103b.

The condenser lens 110a condenses light transmitted the polarization beam splitter 103a. In addition, the condenser lens 110b condenses light transmitted the polarization beam splitter 103b.

Part of light condensed by the condenser lens 110a transits the confocal diaphragm 111a. Moreover, part of light condensed by the condenser lens 110b transits the confocal diaphragm 111b. For example, a pinhole may be used for the confocal diaphragms 111a and 110b. Further, the confocal diaphragms 111a and 110b are respectively arranged at a position conjugate with the fundus Ef.

Light transiting the confocal diaphragm 111a is guided to the photographing device 2. The photographing device 2 comprises a photodetector 2a inside thereof. Moreover, light transiting the confocal diaphragm 111b is guided to the photographing device 3. The photographing device 3 comprises a photodetector 3a inside thereof. The photodetectors 2a and 3a receive the reflected light from the fundus Ef. In the present embodiment, the photodetectors 2a and 3a function as "light receiving units." For example, APD (Avalanche Photodiode), MPPC (Multi-Pixel Photon Counter: registered trademark), or PMT (Photomultiplier Tube) are used as photodetectors.

Embodiment 1

Figure 2:
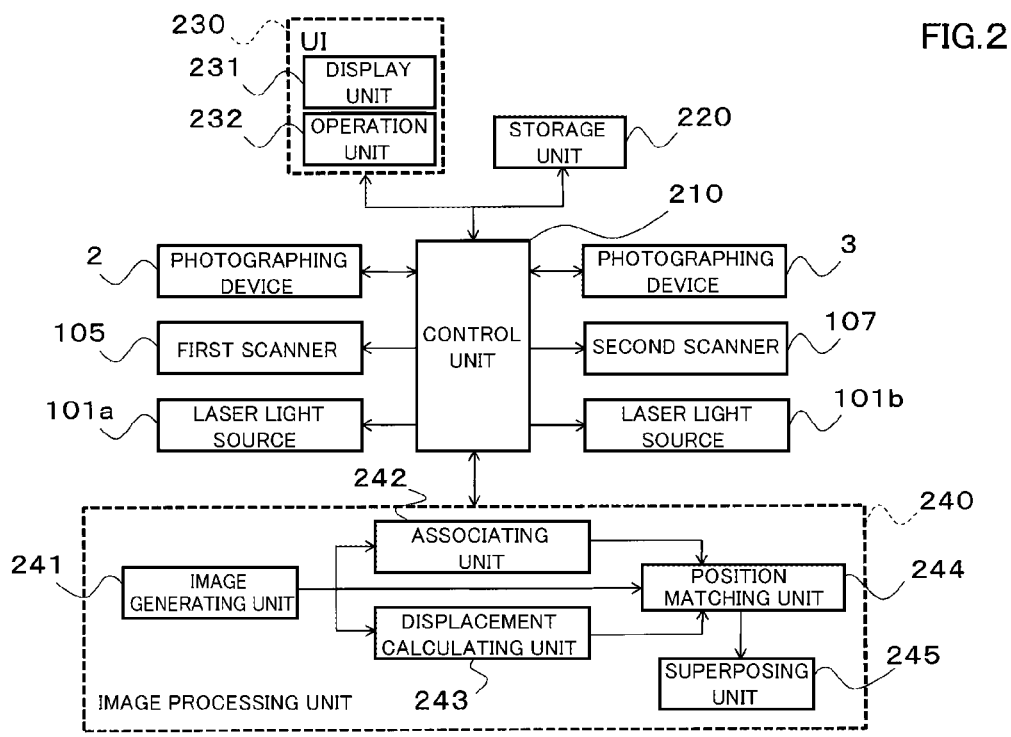
FIG. 2 is a block diagram of a scanning laser ophthalmoscope according to Embodiment 1.
Figure 3:
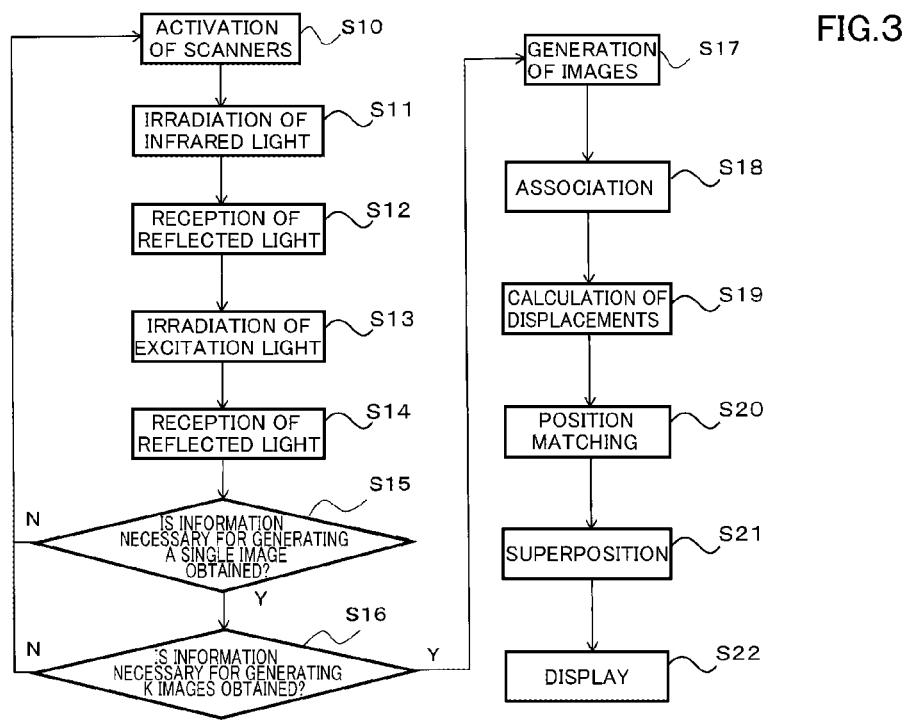
FIG. 3 is a flow chart illustrating an operation of a scanning laser ophthalmoscope according to Embodiment 1.
Figure 4A:
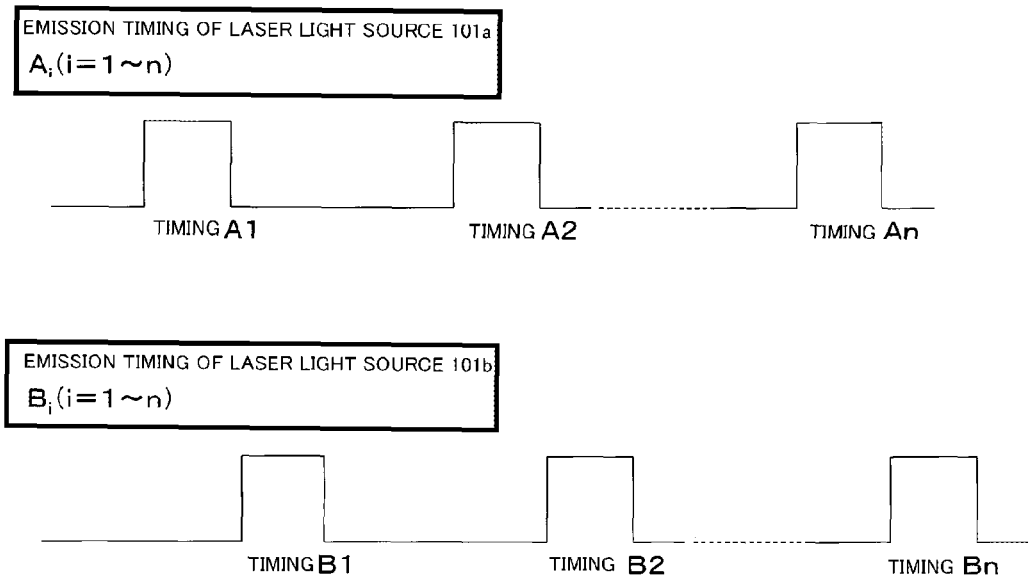
FIG. 4A is a timing chart illustrating an example of an operation of a scanning laser ophthalmoscope according to Embodiment 1.
Figure 4B:
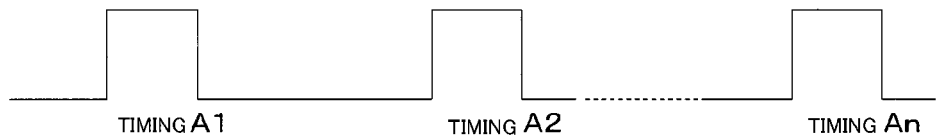
FIG. 4B is a timing chart illustrating an example of an operation of a scanning laser ophthalmoscope according to Embodiment 1.
Figure 4B:
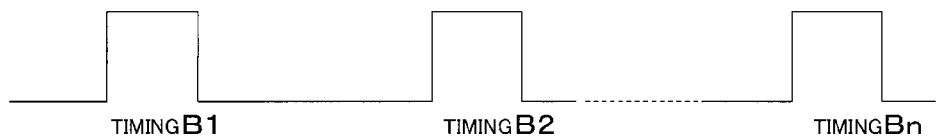

Next, the scanning laser ophthalmoscope according to Embodiment 1 is described using FIGS. 2 to 4.

[Configuration of the Control System]

FIG. 2 is a diagram illustrating the control system of the scanning laser ophthalmoscope 1 according to Embodiment 1. The control system comprises a control unit 210, a storage unit 220, a user interface (UI) 230, and an image processing unit 240.

[Control Unit]

The control unit 210 controls each part of the scanning laser ophthalmoscope 1 according to the present embodiment. For example, the control unit 210 controls the on/off of the laser light sources 101a and 101b. Moreover, the control unit 210 activates the first scanner 105 and the second scanner 107, thereby controlling the two-dimensional scanning of laser light onto the fundus Ef. Moreover, the control unit 210 carries out control for storing images photographed by the photographing devices 2 and 3 in the storage unit 220. Further, the control unit 210 reads image information stored in the storage unit 220 and controls the execution of image processing by the image processing unit 240.

Moreover, the control unit 210 controls the photographing operation by the photographing devices 2 and 3. Specifically, when the laser light source 101a is lit, the photographing device 2 is activated such that the fundus reflected light thereof is received by the photodetector 2a. Meanwhile, when the laser light source 101b is lit, the photographing device 3 is activated such that the fundus reflected light thereof is received by the photodetector 3a.

The control unit 210 comprises, for example, a microprocessor such as a CPU, and an interface for communicating with storage devices such as a RAM, a ROM and a hard disk drive. Computer programs for causing the scanning laser ophthalmoscope 1 to carry out operations characteristic of the present invention are stored in advance in a storage device such as a hard disk drive.

[Storage Unit]

The storage unit 220 stores a variety of information. Specifically, the storage unit 220 stores fundus images photographed by the scanning laser ophthalmoscope 1. Each fundus image is associated with a variety of information such as patient identification information such as a patient ID, left and right eye information that indicates whether the eye E is a left eye or a right eye, information on the photography date and time, types of photography (infrared light photographing, fluorescent photographing, etc.), and photographing conditions (illumination light amount, etc.), which is then stored. Moreover, images obtained by superposing fluorescent images (mentioned later) may also be stored.

[User Interface]

The user interface (UI) 230 is provided with a display unit 231 and an operation unit 232.

[Display Unit]

The display unit 231 is controlled by the control unit 210 to display various screens and information. The display unit 231 comprises any display device such as an LCD (Liquid Crystal Display). The display unit 231 may comprise a display device provided on the scanning laser ophthalmoscope 1.

[Operation Unit]

The operation unit 232 is used by operators for operating the scanning laser ophthalmoscope 1. The operation unit 232 may include an operation device and an input device displayed by the display unit 231 such as a GUI (Graphical User Interface) such as an operation key and an operation button. Moreover, the operation unit 232 may include an operation device and an input device such as a keyboard and a mouse.

[Image Processing Unit]

The image processing unit 240 comprises an image generating unit 241, an associating unit 242, a displacement calculating unit 243, a position matching unit 244, and a superposing unit 245.

The image generating unit 241 functions to generate a first image based on a light reception result of reflected light of first laser light, and functions to generate a second image based on light reception result of reflected light of second laser light. In the present embodiment, the first image is an infrared image and the second image is a fluorescent image obtained by photographing fluorescence generated by excitation light.

The associating unit 242 functions to carry out the processing of associating the first image generated by the image generating unit 241 and the second image photographed in parallel with the first image. The first image and the second image to be associated by the associating unit 242 are images obtained based on the parallelly scanned (mentioned later) first laser light and second laser light. Details on the associating process are mentioned later. Further, "photographing" refers to a series of laser light scanning and the light receiving action of fundus reflected light for generating images.

The displacement calculating unit 243 functions to calculate displacements between images regarding the multiple first images generated by the image generating unit 241. Details on the displacement calculation are mentioned later.

The position matching unit 244 functions to match the positions of the multiple second images generated by the image generating unit 241 based on the processing result from the associating unit 242 and the displacements calculated by the displacement calculating unit 243. Details on position matching are mentioned later.

The superposing unit 245 functions to superpose the multiple second images that have undergone the position matching. The images superposed by the superposing unit 245 are displayed on the display unit 231 as static images or dynamic images.

[Operation of Embodiment 1]

The operation of the scanning laser ophthalmoscope 1 according to Embodiment 1 is explained with reference to FIGS. 3 and 4. In the present embodiment, the case of displaying a static image is described.

In the present embodiment, a series of operations for superposing and displaying fluorescent images is described. It is assumed that a fluorescent agent such as fluorescein has been intravenously injected into the patient in advance. It should be noted that the following operation may also be applied for observing autofluorescence.

The scanning laser ophthalmoscope 1 scans the fundus Ef with multiple scanning points $P_{ij}$ (i=1 to M, j=1 to N), and forms a single image based on the reflected light obtained from the respective scanning points $P_{ij}$.

In response to an instruction to commence photographing from the operation unit 232, etc., the control unit 210 activates the first scanner 105 and the second scanner 107 in order to match the positions thereof with respect to one point ($P_{11}$) of the fundus Ef at which the infrared light from the laser light source 101a as well as the excitation light from the laser light source 101b are irradiated (S10).

Next, the infrared light from the laser light source 101a is irradiated onto $P_{11}$ using the first scanner 105 and the second scanner 107 (S11). Then, the photodetector 2a receives the fundus reflected light of the infrared light irradiated at S11 (S12).

In the same manner, the excitation light from the laser light source 101b is irradiated onto the same position ($P_{11}$) as the position of the fundus Ef irradiated with the infrared light at S11 using the first scanner 105 and the second scanner 107 (S13). Then, the photodetector 3a receives the fundus reflected light (agent fluorescence) generated by the excitation light irradiated at S13 (S14).

Operations S11 to S14 are repeated until the information necessary for generating a single image (one each of an infrared image and a fluorescent image) is obtained (from $P_{11}$ to $P_{MN}$. S15: Y). In the event that the information necessary for generating a single image has not been able to be obtained (S15: N), the first scanner 105 and the second scanner 107 are activated (scans) by the control unit 210, and the same operations as S11 to S14 are carried out at positions different from the previously photographed position.

FIG. 4A is a timing chart illustrating the emission timings of the laser light source 101a and laser light source 101b. Here, the timings at which the laser light source 101a (infrared light) is lit with respect to the two-dimensionally arranged scanning points $P_{ij}$ are denoted by $A_i$ (i=1 to n. n=M×N), while the emission timings of the laser light source 101b (excitation light) is lit at almost the same timing as $A_i$ are denoted by $B_i$ (i=1 to n. n=M×N). Moreover, the reflected lights based on the laser light emitted at timing $A_i$ and timing $B_i$ are received by the photodetectors 2a and 3a at substantially the same timing. Then, the image generating unit 241 generates a first image $G_1$ based on the reflected lights based on the laser lights irradiated at timings $A_1$ to $A_n$. Moreover, the image generating unit 241 generates a second image $H_1$ based on the reflected lights based on the laser lights irradiated at timings $B_1$ to $B_n$. That is, in the present embodiment, it may be said that the first image $G_1$ and the second image $H_1$ are images "photographed based on the parallelly scanned first laser light and second laser light."

It should be noted that the emission timings of the laser light source 101a and the laser light source 101b are not limited to those illustrated in FIG. 4A. It is also possible to set the timings $A_i$ (i=1 to n. n=M×N) of emitting the laser light source 101a (infrared light) and the timings $B_i$ (i=1 to n. n=M×N) of emitting the laser light source 101b (excitation light) to be the same. In this case, the reflected lights based on the laser lights emitted at a timing $A_i$ and a timing $B_i$ are respectively received by the photodetectors 2a and 3a at the same timing. Then, the image generating unit 241 generates the first image $G_1$ based on the reflected lights based on the laser lights emitted at timings $A_1$ to $A_n$. Moreover, the image generating unit 241 generates the second image $H_1$ based on the reflected lights based on the laser lights emitted at timings $B_1$ to $B_n$. That is, in this case as well, it may be said that the first image $G_1$ and the second image $H_1$ are images "photographed based on the parallelly scanned first laser light and second laser light."

In this manner, in the present embodiment, "parallelly" refers to "substantially (almost) the same time." "Substantially" allows a time lag in which the measurement of the same scanning point $P_{ij}$ for the first image $G_k$ and the second image $H_k$ is possible without eye movement.

Further, once information necessary for generating the 1st images are obtained at timings $A_i$ (i=1 to n) and $B_i$ (i=1 to n) (that is, after scanning from $P_{11}$ to $P_{MN}$ is completed), in order to obtain information necessary for generating the 2nd images, $P_{11}$ to $P_{MN}$ are scanned again at timings $A_i$ (i=1 to n) and timings $B_i$ (i=1 to n) (S10 to S15). The image generating unit 241 generates the first image $G_2$ and the second image $H_2$ by receiving the fundus reflected light obtained based on this 2nd scanning. In this case, the first image $G_2$ and the second image $H_2$ correspond to images "photographed based on the parallelly scanned first laser light and second laser light."

The operations S11 to S14 are repeated in this manner, and when photographing of a certain photographing range ($P_{11}$ to $P_{MN}$) with a predetermined number of times (for example, 40 times) is completed (Y at S16), image processing is carried out by the image processing unit 240. On the other hand, in the event that photographing of the predetermined number of times has not been completed (N at S16), the first scanner 105 and the second scanner 107 are activated by the control unit 210 (S10), and photographing is continued upon returning to $P_{11}$ (S11 to S14).

In the case of "Y" at S16, the image generating unit 241 generates multiple infrared images based on the fundus reflected lights received by the photodetector 2a. Moreover, the image generating unit 241 generates multiple fluorescent images based on the fundus reflected lights (agent fluorescence) received by the photodetector 3a (S17).

Next, the associating unit 242 associates the infrared image and the fluorescent image generated at S16 (S18). For example, the associating unit 242 executes the association so that the infrared image $G_1$ and the fluorescent image $H_1$ based on the reflected lights received at substantially the same timing (that is, "parallelly photographed") are coupled. The associating unit 242 carries out this association regarding all photographed images. Thereby, the first image $G_k$ and the second image $H_k$ are associated (k=1 to K; K indicates the number of images).

Moreover, the displacement calculating unit 243 calculates the displacements between the multiple infrared images generated at S16 (S19). Specifically, for example, the displacement calculating unit 243 compares the position of the distinctive area α (papilla, blood vessel, vascular bifurcation, lesions, etc.) in the frame of the infrared image $G_1$ and the position of the distinctive area α in the frame of the infrared image $G_k$ (k≥2), and calculates the displacement thereof. In this process, the respective displacements of the infrared image $G_2$ to $G_K$ with respect to the infrared image $G_1$ which is set as a standard. It should be noted that S18 and S19 are not required to be carried out in this order. Moreover, the processes of S18 and S19 may be carried out simultaneously.

Next, the position matching unit 244 matches the positions between the fluorescent images based on the processing result of S18 and the displacement calculated at S19 (S20). Specifically, when the displacement between the infrared image $G_1$ and the infrared image $G_k$ (k≥2) is β, it is assumed that the displacement of the fluorescent image $H_k$ with respect to the fluorescent image $H_1$ is also β. This assumption may be appropriate from the fact that the infrared image $G_1$ and the fluorescent image $H_1$ photographed almost simultaneously are associated, and the infrared image $G_k$ and the fluorescent image $H_k$ photographed almost simultaneously are associated by the associating unit 242. Thus, the position matching unit 244 performs position matching by processing of shifting the fluorescent image $H_k$ with respect to fluorescent image $H_1$ by the displacement −β. A known image correction processing method such as the affine transformation is used for the position matching. It should be noted that when the size of a distinctive area is different due to pulsations, etc., it is possible to carry out processing to match the size of the fluorescent image $H_2$ with respect to the size of the fluorescent image $H_1$. In the present embodiment, it is assumed that such differences in size of distinctive areas are included in the "displacement."

Regarding the multiple fluorescent images $H_k$ that have undergone the position matching at S20, the superposing unit 245 superposes the fluorescent images $H_k$ to form a single static image (S21). Subsequently, the fluorescent image superposed by the superposing unit 245 is displayed on the display unit 231, thereby allowing a tester to observe the fluorescent image (S22).

[Action and Effect of Embodiment 1]

According to the present embodiment, it becomes possible to two-dimensionally scan the first laser light and second laser light, respectively, onto the fundus of the eye using the first scanner 105 and the second scanner 107, while emitting first laser light and second laser light with different wavelengths from each other by the laser light sources 101*a* and 101*b*. Moreover, the reflected lights of the first laser light and the second laser light are respectively received by the photodetectors 2*a* and 3*a*, thereby the image generating unit 241 is capable of generating first images and second images. Further, the associating unit 242 is capable of associating the first images and the second images based on the first laser light and second laser light parallelly scanned using the first scanner 105 and the second scanner 107. Moreover, the displacement calculating unit 243 is capable of carrying out the process of calculating the displacement between the multiple first images. Then, the position matching unit 244 matches the position between the multiple second images based on the processing result from the associating unit and the displacement, and the superposing unit 245 superposes the multiple second images that have undergone position matching. Accordingly, it becomes possible to display the images obtained by superposing the multiple second images on the display unit 231.

Particularly in the present embodiment, infrared light is used as the first laser light and excitation light is used as the second laser light. Then, the second image is a fluorescent image based on the light reception result from the light receiving unit of the fluorescence generated by the excitation light.

In this manner, according to the present embodiment, the positions between the second images may be matched based on the displacement between the multiple first images by associating the parallelly photographed first images and second images. Thus, even when commencing photographing under pitch-dark conditions such as fluorescent images for observing running vessels or when weak fluorescence is photographed multiple times, the fluorescent images may be accurately superposed. Moreover, the fluorescent images may be accurately superposed without the effects of eye movement, pulsations, etc.

Moreover, in the present embodiment, a configuration is taken in which the laser light sources 101*a* and 101*b* alternately emit the first laser light and the second laser light.

By means of configuring in this manner, the scanning laser ophthalmoscope 1 may be activated with a smaller peak electric energy than constant luminescence (continuous luminescence) of the laser light sources 101*a* and 101*b*. Further, simplification of the hardware configuration becomes possible because one photographic optical system can be used in a time-division fashion.

Embodiment 2

Next, the scanning laser ophthalmoscope 1 according to Embodiment 2 is described with reference to FIG. 5 and FIG. 6. Many configurations of the scanning laser ophthalmoscope 1 according to Embodiment 2 are the same as that of Embodiment 1, so the points differing from Embodiment 1 are mainly described.

Regarding the fluorescent image photographing using fluorescent agents such as fluorescein, etc., there are cases in which the state of the fluorescent agent spreading in the fundus of the subject is photographed after the fluorescent agent is intravenously injected into the subject. The timings in this photographing are classified into, for example, an "early period," a "medium period," and a "late period." Further, there are various definitions of the "early period," "medium period," and "late period;" however, in the following, the definition with a focus on "luminance of the image" is used for convenience.

The "early period" refers to the period of time from the moment of intravenously injecting the fluorescent agent into the subject until the fluorescent agent spreads and diffuses into the fundus. During this period, the fluorescence intensity is of a degree such that the distinctive areas (papilla, blood vessel, vascular bifurcation, lesions, etc.) cannot be recognized.

The "medium period" refers to the period of time in which the fluorescent agent spreads and diffuses into the fundus, allowing fluorescent images to be obtained based on the excitation light. In this period, the fluorescence intensity is generally of a degree such that the distinctive areas may be sufficiently recognized.

The "late period" refers to the period of time in which the lifespan of the fluorescence of the fluorescent agent comes to an end and the fluorescence obtained by the excitation light starts to attenuate to the period in which the emission of fluorescence terminates. In this period, the fluorescence intensity is of a degree such that the distinctive areas may not be sufficiently recognized.

In this manner, particularly regarding the fluorescent images photographed in the early period and late period, it is difficult to recognize the distinctive areas in the images. That is, in the early period and late period, the fluorescent image cannot be accurately superposed unless other images such as the infrared image, etc. are used.

Meanwhile, in the medium period, the distinctive areas may be recognized by the fluorescent image alone. Accordingly, by means of matching the positions of the images based on the displacements of the distinctive areas when superposing, accurate superposition of the images becomes possible without using other images. Further, associations with other images, etc. become unnecessary; therefore, efficiency of the superposition of images may be improved.

In the present embodiment, a configuration of accurately and efficiently realizing superposition of images by changing processes in correspondence with the difference in fluorescence intensity is described.

[Configuration of the Control System]

Figure 5:
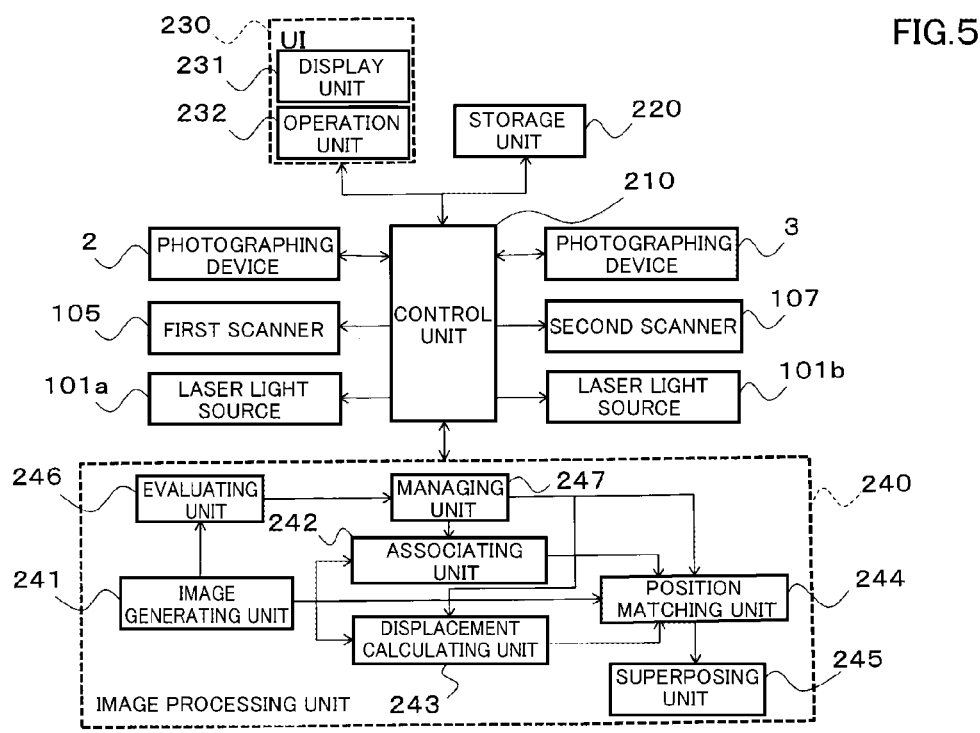
FIG. 5 is a block diagram of a scanning laser ophthalmoscope according to Embodiment 2.
Figure 6:
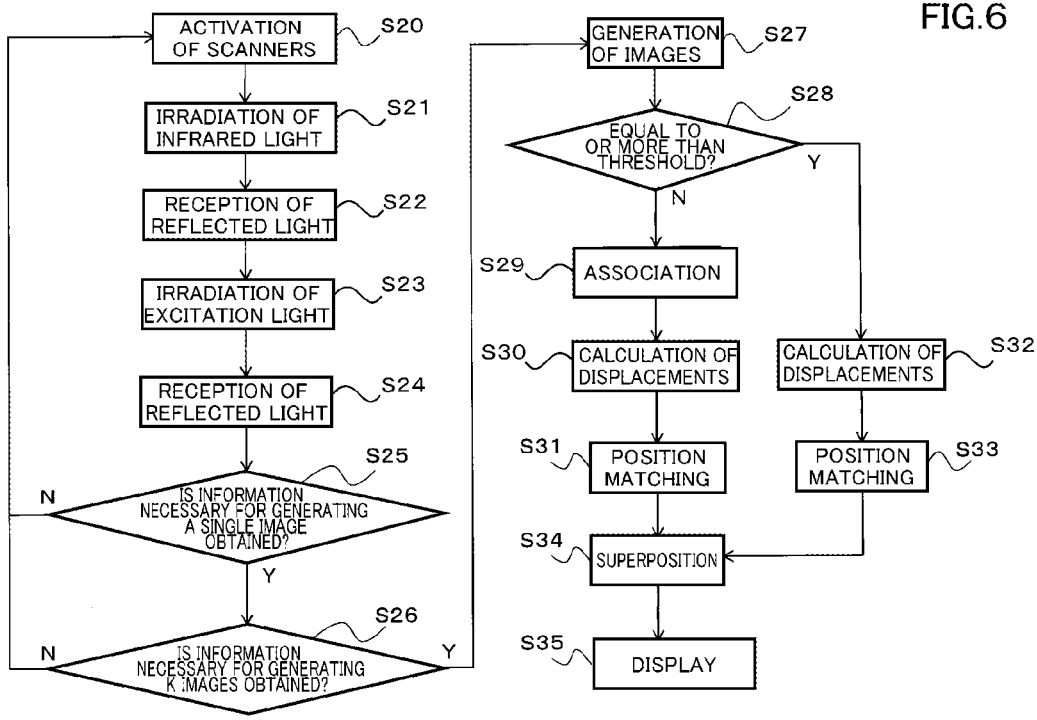
FIG. 6 is a flow chart illustrating an operation of a scanning laser ophthalmoscope according to Embodiment 2.

FIG. 5 is a diagram illustrating the control system of the scanning laser ophthalmoscope according to Embodiment 2. The control system comprises a control unit 210, a storage unit 220, a user interface (UI) 230, and an image processing unit 240. Descriptions of the control unit 210, the storage unit 220, and the user interface (UI) 230 are omitted as they have the same configuration as that of Embodiment 1.

[Image Processing Unit]

The image processing unit 240 comprises an evaluating unit 246 and a managing unit 247 in addition to the image generating unit 241, the associating unit 242, the displacement calculating unit 243, the position matching unit 244, and the superposing unit 245 in Embodiment 1.

The evaluating unit 246 functions to evaluate the luminance of the second image generated by the image generating unit 241. Here, "luminance of the second image" refers to the luminance distribution of the image generated by the image generating unit 241 or the luminance values in the distinctive area of the image generated by the image generating unit 241. Details on the evaluating process by the evaluating unit 246 are described later.

The managing unit 247 functions to switch whether or not processing is performed by at least any from among the associating unit 242, the displacement calculating unit 243, and the position matching unit 244 based on the evaluation result from the evaluating unit 246. Details thereof are mentioned later.

[Operation of Embodiment 2]

The operation of the scanning laser ophthalmoscope 1 according to Embodiment 2 is described with reference to FIG. 6. It should be noted that, in the present embodiment, a case of displaying a static image is described.

In the present embodiment, a series of operations of superposing and displaying fluorescent images are described.

When a fluorescent agent such as fluorescein, etc. is intravenously injected into the subject and an instruction for commencing photographing are given from the operation unit 232, etc., the control unit 210 activates the first scanner 105 and the second scanner 107, and matches the positions of the infrared light from the laser light source 101a and the excitation light from the laser light source 101b to a certain point ($P_{11}$) of the fundus Ef to be irradiated (S20).

Next, the infrared light from the laser light source 101a is irradiated onto $P_{11}$ using the first scanner 105 and the second scanner 107 (S21). Then, the photodetector 2a receives the fundus reflected light of the infrared light irradiated at S21 (S22).

In the same manner, the excitation light from the laser light source 101b is irradiated onto the same position ($P_{11}$) as the position of the fundus Ef irradiated with the infrared light at S21 using the first scanner 105 and the second scanner 107 (S23). Then, the photodetector 3a receives the fundus reflected light (agent fluorescence) generated by the excitation light irradiated at S23 (S24). The emission timings of the laser light source 101a and the laser light source 101b are the same as in Embodiment 1, so descriptions thereof are omitted.

The operations S21 to S24 are repeated until the information necessary for generating a single image (one each of an infrared image and a fluorescent image) is obtained (from $P_{11}$ to $P_{MN}$. S25: Y). In the event that the information necessary for generating a single image has not been obtained (S25: N), the first scanner 105 and the second scanner 107 are activated (scans) by the control unit 210 (S20), and the same operations S21 to S24 are carried out at positions different from the previously photographed position.

Further, once the information necessary for generating the 1st images is obtained from timings $A_i$ (i=1 to n) and $B_i$ (i=1 to n) (after scanning from $P_{11}$ to $P_{MN}$ is completed), in order to obtain information necessary for generating the 2nd images, $P_{11}$ to $P_{MN}$ are scanned again at timings $A_i$ (i=1 to n) and timings $B_i$ (i=1 to n) (S20 to S25). The image generating unit 241 generates the first image $G_2$ and the second image $H_2$ by receiving the fundus reflected light obtained based on this second scanning. In this case, the first image $G_2$ and the second image $H_2$ corresponds to the images "photographed based on the parallelly scanned first laser light and second laser light."

The operations S21 to S24 are repeated in this manner, and when photographing of the certain photographing range ($P_{11}$ to $P_{MN}$) with the predetermined number of times is completed (Y at S26), image processing is carried out by the image processing unit 240. On the other hand, when photographing of the predetermined number of times is not completed (N at S26), the first scanner 105 and the second scanner 107 are activated by the control unit 210 (S20), and photographing is continued after returning to $P_{11}$ (S21 to S24).

In the case of "Y" at S26, the image generating unit 241 generates multiple infrared images based on the fundus reflected lights received by the photodetector 2a. Moreover, the image generating unit 241 generates multiple fluorescent images based on the fundus reflected lights (agent fluorescence) received by the photodetector 3a (S27).

Next, regarding one fluorescent image generated at S27, the evaluating unit 246 compares, for example, the maximum luminance value in the distinctive area of the image with the predetermined threshold (S28). The predetermined threshold may be determined based on, for example, the average luminance from general clinical data photographed in the past, or the luminance in a previous image of this subject, etc.

Here, when it is determined that the maximum luminance value in the distinctive area of the fluorescent image generated at S27 is the same as the threshold or less (N at S28), it is highly likely that the distinctive area will not be recognized in the fluorescent image (this is thought to take place in the "early period" or the "late period"). In this case, the positions of the fluorescent images should be matched based on the infrared images in the same manner as Embodiment 1. Accordingly, based on the evaluation result from the evaluating unit 246, the managing unit 247 instructs the associating unit 242 to carry out the associating process.

The associating unit 242 associates the infrared images and the fluorescent images generated in S27 based on the instruction (S29). Moreover, the displacement calculating unit 243 calculates the displacements between the multiple infrared images generated at S27 based on the instruction from the managing unit 247 (S30). Then, in response to the instruction from the managing unit 247, the position matching unit 244 matches the positions of the fluorescent images based on the processing result of S29 and the displacements calculated at S30 (S31). The detailed processing method of these steps is the same as Embodiment 1, so detailed descriptions are omitted.

Meanwhile, when it is determined that the maximum luminance value in the distinctive area of the fluorescent image generated at S27 is the same as the threshold or more (Y at S28), it is highly likely that the distinctive area will be recognized on the fluorescent image (this is thought to take place in the "medium period"). In this case, position matching is possible by the fluorescent images alone without being based on the displacements of the infrared images. Accordingly, the managing unit 247 instructs the associating unit 242 to stop (so as not to execute) the associating process based on the evaluation result from the evaluating unit 246.

In this case, the displacement calculating unit 243 carries out the process of calculating the displacements between the multiple fluorescent images generated at S27 based on the instruction from the managing unit 247 (S32). Then, the position matching unit 244 matches the positions between the fluorescent images using the displacements calculated at S32 based on the instructions from the managing unit 247 (S33).

Regarding the multiple fluorescent images that have undergone position matching at S31 or S33, the superposing unit 245 superposes these fluorescent images to form a single static image (S34). Subsequently, the tester is capable of observing the desired fluorescent images due to the fluorescent images superposed at the superposing unit 245 being displayed on the display unit 231 (S35).

[Action and Effect of Embodiment 2]

According to the present embodiment, the evaluating unit 246 compares the state (luminance) of the second image with the predetermined threshold. Then, based on the evaluation result from the evaluating unit 246, the managing unit 247 carries out the instruction to commence and/or stop the processing by the associating unit 242, displacement calculating unit 243, and the position matching unit 244.

In this manner, according to the present embodiment, the fluorescent images may be accurately superposed because it is determined whether to carry out the associating process or omit the associating process depending on the condition of the second image, efficiency of image superposition can be improved because a part of the image processing is omitted in accordance with the luminance of the fluorescent image.

[Modified Example of Embodiment 2]

Regarding the action of switching the process of each part in the "early period," the "medium period," and the "late period", for example, it is possible for the managing unit 247 to carry out operation switching upon the user giving instructions for switching by manual input while looking at the image. Alternatively, it is also possible to calculate the average time from the "early period" to the "medium period" and the average time from the "medium period" to the "late period" based on general clinical data or past data of this subject, and to automatically carry out operation switching by the managing unit 247 based on these average times.

Moreover, regardless of the evaluation result from the evaluating unit 246, the associating unit 242 may continuously carry out the associating process. By means of continuously carrying out the associating process in this manner, for example, even when the fluorescent images in which the distinctive area cannot be recognized are obtained in the "medium period," it becomes possible to switch to the position matching process of the fluorescent images $H_k$ using the infrared images $G_k$. Accordingly, when photographing the state of the fluorescent agent spreading in the fundus in real-time, the real-time properties are not missed.

Embodiment 3

Next, the scanning laser ophthalmoscope 1 according to Embodiment 3 is described with reference to FIG. 7 and FIG. 8. Many configurations of the scanning laser ophthalmoscope 1 according to Embodiment 3 are the same as those of Embodiments 1 and 2, so descriptions are mainly given regarding points that are different from Embodiments 1 and 2.

When taking eye movements such as involuntary eye movement into consideration, the larger the scanning region of the fundus becomes, the greater the possibility becomes for the generation of image distortion. Particularly, there is a danger of large distortion occurring between images in the vicinity of the position at which scanning is commenced and images in the vicinity of the position at which scanning terminates.

When position matching of the entire image distorted in this manner is carried out with a certain standard (for example, the distinctive area α of Embodiment 1), there are times in which the position matching reliability of the image of the area desired to be observed deteriorates when the distinctive area α is distanced from the area desired to be observed. Moreover, when position matching is carried out at the multiple distinctive areas α1 to αn, the positions of these distinctive areas are comprehensively matched (for example, the positions are matched such that the total misregistration of the all distinctive areas becomes minimal), resulting in the possible deterioration of the position matching reliability of the area desired to be observed.

In the present embodiment, a configuration is described in which the positions are matched focusing on the image region corresponding to the area desired to be observed, thereby allowing position matching of the area desired to be observed with high accuracy. It should be noted that in the following embodiments, the "image region corresponding to the area desired to be observed" may be referred to as "the subregion."

[Configuration of the Control System]

Figure 7:
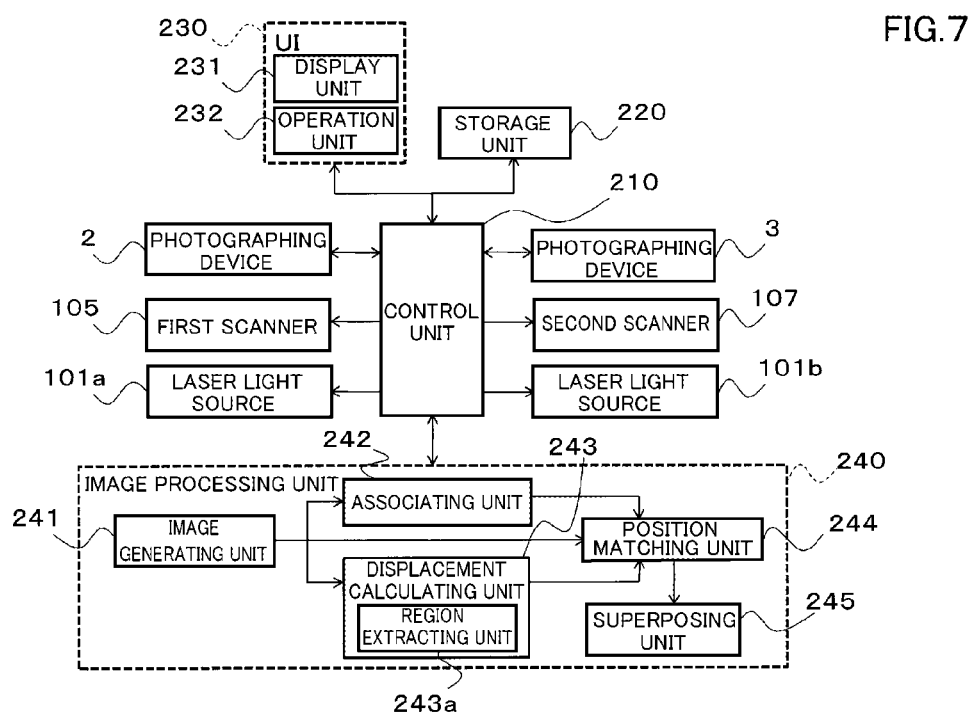
FIG. 7 is a block diagram of a scanning laser ophthalmoscope according to Embodiment 3.
Figure 8:
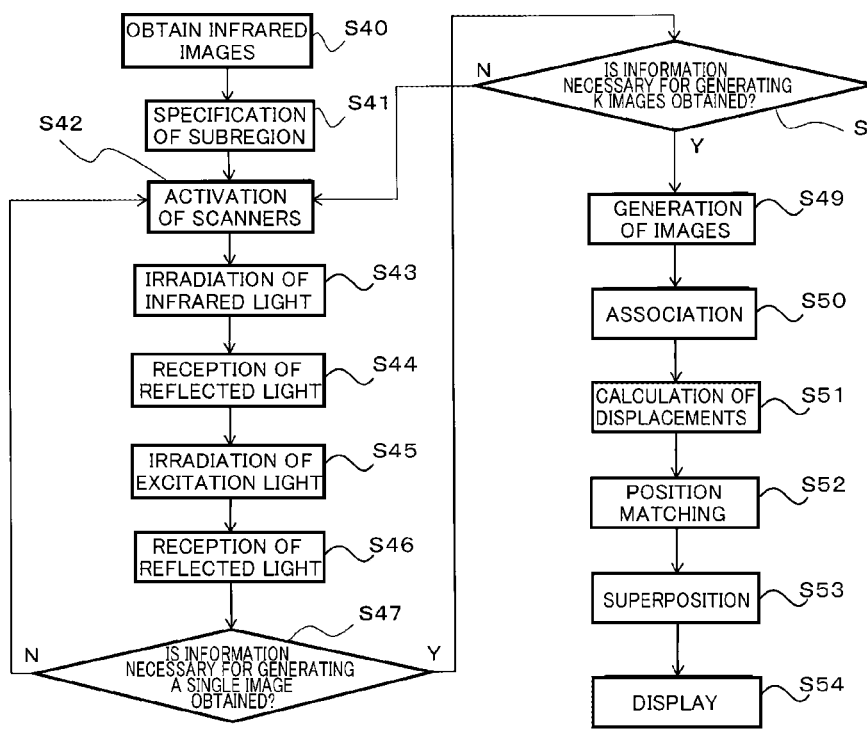
FIG. 8 is a flow chart illustrating an operation of a scanning laser ophthalmoscope according to Embodiment 3.

FIG. 7 is a diagram illustrating the control system of the scanning laser ophthalmoscope according to Embodiment 3. The control system comprises a control unit 210, a storage unit 220, a user interface (UI) 230, and an image processing unit 240. Descriptions on the control unit 210, the storage unit 220, and the user interface (UI) 230 are omitted because the configuration thereof is the same as Embodiments 1 and 2.

[Image Processing Unit]

The image processing unit 240 comprises a region extracting unit 243a in addition to the image generating unit 241, the associating unit 242, the displacement calculating unit 243, the position matching unit 244, the superposing unit 245 in Embodiment 1. Hereinafter, a description is provided when the subregion of the first image is considered, but as mentioned later, this is the same when the second image or previous image (color fundus image, etc.) is considered.

The displacement calculating unit 243 of the present embodiment functions to specify the subregion in the first image. Moreover, the displacement calculating unit 243 functions to calculate the displacements between images within the subregions of the multiple first images. Details on the specification of the subregion and details on calculating the displacements are mentioned later.

The region extracting unit 243a is provided as a part of the displacement calculating unit 243. The region extracting unit 243a functions to respectively extract the subregions of the first image and the second image that are associated by the associating unit 242. Specifically, for example, a process is carried out whereby an image is extracted of coordinate values corresponding to other first image and second image based on the coordinate values of the image in the subregion of a certain first image specified by the displacement calculating unit 243. The displacement calculating unit 243 calculates the displacements between images within the subregions of the first images extracted by the region extracting unit 243a.

It should be noted that when obtaining the subregion of other first image corresponding to the subregion of a certain first image, the displacement calculating unit 243 carries out pattern matching of the subregion of a certain first image with respect to the other first image. As a result, the subregion of the other first image corresponding to the subregion of a certain image may be specified.

The position matching unit 244 according to the present embodiment functions to match the positions of images within the subregions of the second images extracted by the region extracting unit 243a based on the displacements between images within the subregions of the first images calculated by the displacement calculating unit 243. Details on position matching are mentioned later.

[Operations of the Embodiment 3]

Operations of the scanning laser ophthalmoscope 1 according to Embodiment 3 are described with reference to FIG. 8. It should be noted that the static images are displayed in the present embodiment.

In the present embodiment, a series of operations for superposing and displaying the fluorescent images are described. It is assumed that a fluorescent agent such as fluorescein is intravenously injected into the patient in advance. Further, the following operations may also be applied for observing autofluorescence.

The scanning laser ophthalmoscope 1 scans the fundus Ef with multiple scanning points $P_{ij}$ (i=1 to M, j=1 to N), and forms a single image based on the reflected lights obtained from the respective scanning points $P_{ij}$.

First, the first scanner 105 and the second scanner 107 scan the fundus Ef ($P_{ij}$ (i=1 to M, j=1 to N)) with the infrared light from the laser light source 101a based on the instructions from the operation unit 232, etc., to obtain the infrared image (S40). The infrared images are generated by the image generating unit 241. Images at alignment and images at preliminary observation prior to fluorescent photographing may also be used as the infrared image. Further, the infrared image obtained near the beginning when photographing using the scanning laser ophthalmoscope 1 may also be used.

Next, the displacement calculating unit 243 analyzes the infrared image obtained at S40, and specifies the subregion corresponding to the distinctive areas γ (for example, the papilla, macula, or areas suspected of having lesions such as accumulation of blood vessels, etc.) in this infrared image (S41). Specifically, the displacement calculating unit 243 compares the luminance distribution of the pixels of the infrared image and the general luminance distribution in the papilla, the macula, etc., obtains the coordinate values corresponding to the area (distinctive area γ) in which the luminance distributions coincide, and specifies the range of these coordinate values as the subregion. Alternatively, it is capable of setting the distinctive area γ by determining a distinctive area (for example, determining a "bright circular area"="papilla") in the luminance distribution of the pixels in the infrared image, obtaining the coordinate values corresponding to this, and specifying the range of these coordinate values as the subregion.

Subsequently, the control unit 210 activates the first scanner 105 and the second scanner 107 based on instructions to commence photographing from the operation unit 232, etc., then matches the positions thereof with respect to one point ($P_{11}$) of the fundus Ef at which the infrared light from the laser light source 101a as well as the excitation light from the laser light source 101b are irradiated (S42).

Next, the infrared light from the laser light source 101a is irradiated onto $P_{11}$ by the first scanner 105 and the second scanner 107 (S43). Then, the photodetector 2a receives the fundus reflected light of the infrared light irradiated at S43 (S44).

In the same manner, the excitation light from the laser light source 101b is irradiated onto the same position ($P_{11}$) as the position of the fundus Ef irradiated with the infrared light at S43 using the first scanner 105 and the second scanner 107 (S45). Then, the photodetector 3a receives the fundus reflected light (agent fluorescence) generated by the excitation light irradiated at S45 (S46).

Operations S43 to S46 are repeated until the information necessary for generating a single image (one each of an infrared image and a fluorescent image) is obtained (from $P_{11}$ to $P_{MN}$. S47: Y). In the event that the information necessary for generating a single image has not been obtained (S47: N), the first scanner 105 and the second scanner 107 are activated (scans) by the control unit 210 (S42), and the same operations S43 to S46 are carried out at positions different from the previously photographed position.

Operations S43 to S46 are cyclically repeated in this manner while sequentially changing the scanning points $P_{ij}$, and once photographing of a certain photographing range ($P_{11}$ to $P_{MN}$) with a predetermined number of times (for example, 40 times) is completed (Y at S48), image processing is carried out by the image processing unit 240. Meanwhile, in the event that photographing the predetermined number of times has not been completed (N at S48), the first scanner 105 and the second scanner 107 are activated by the control unit 210 (S42), and photographing is continued upon returning to $P_{11}$ (S43 to S46).

In the case of "Y" at S48, the image generating unit 241 generates multiple infrared images based on the fundus reflected light received by the photodetector 2a. Moreover, the image generating unit 241 generates multiple fluorescent images based on the fundus reflected light (agent fluorescence) received by the photodetector 3a (S49).

Next, the associating unit 242 associates the infrared image and the fluorescent image generated at S49 (S50). For example, the associating unit 242 associates the infrared image $G_1$ and the fluorescent image $H_1$ based on the reflected lights received at substantially the same timing (that is, "parallelly photographed"). The associating unit 242 carries out this association regarding all photographed images. Thereby, the first image $G_k$ and the second image $H_k$ are associated (k=1 to K; K indicates the number of images).

The displacement calculating unit 243 calculates the displacements between the multiple infrared images generated at S49 (S51). For this purpose, in the present embodiment, the region extracting unit 243a extracts the subregions of the infrared image $G_k$ and the fluorescent image $H_k$ associated at S50, respectively, based on the coordinate values of the images within the subregions specified at S41. Specifically, for example, pattern matching of the subregions specified at S41 is carried out with respect to the first image in order to specify the subregions in the first image (the coordinate values of the subregions). Next, regarding the second image associated with this first image, the image with the pixels of the same coordinate values as the subregion of this first image is extracted as "the image of the subregion." Subsequently, the displacement calculating unit 243 compares the subregion in the frame of the infrared image $G_1$ and the subregion in the frame of the infrared image $G_k$ (k≥2), and calculates the displacement thereof. This process obtains, for example, the respective displacements of the infrared image $G_2$ to $G_K$ with respect to the infrared image $G_1$ that is the standard.

Next, the position matching unit 244 matches the positions between the fluorescent images based on the processing result of S50 and the displacements calculated at S51 (S52). Specifically, when the displacements of the subregion in the infrared image $G_k$ (k≥2) with respect to the subregion in the infrared image $G_1$ is δ, it is assumed that the displacement of fluorescent image $H_k$ with respect to fluorescent image $H_1$ is also δ. This assumption may be appropriate from the fact that the infrared image $G_1$ and the fluorescent image $H_1$ photographed almost simultaneously are associated, while the infrared image $G_k$ and the fluorescent image $H_k$ photographed almost simultaneously are associated by the associating unit 242. Thus, the position matching unit 244 performs position matching by processing of shifting the fluorescent image $H_k$ with respect to the fluorescent image $H_1$ by a displacement −β.

Regarding the multiple fluorescent images $H_k$ that have undergone position matching at S52, the superposing unit 245 superposes the fluorescent images $H_k$ in order to form a single static image (S53). Subsequently, the fluorescent image superposed at the superposing unit 245 is displayed on the display unit 231, thereby allowing a tester to observe the fluorescent image (S54).

[Action and Effect of Embodiment 3]

According to the present embodiment, the displacement calculating unit 243 calculates the displacements between images within the subregions regarding the images within the subregion of the first image.

Further, according to the present embodiment, the displacement calculating unit 243 comprises the region extracting unit 243a that extracts the subregions in the first image and the second image. Further, the displacement calculating unit 243 calculates the displacements between images within the subregions regarding images within the subregions of the multiple first images extracted by the region extracting unit 243a. Moreover, the position matching unit 244 matches the positions of images within the subregions of the second images extracted by the region extracting unit 243a based on the displacements calculated by the displacement calculating unit 243.

Further, according to the present embodiment, the displacement calculating unit 243 analyzes the first image (infrared image) to specify a partial region thereof, and specifies the region in the first image corresponding to the partial region as the subregion.

In this manner, according to the present embodiment, the area desired to be observed (distinctive area) is specified from the infrared image (first image), and the fluorescent images are superposed based on the displacements between the subregions corresponding to this distinctive area. This allows position matching of the area desired to be observed with high accuracy by matching the positions focusing on the subregions corresponding to the area desired to be observed.

[Modified Example of Embodiment 3]

In Embodiment 3, a case is explained regarding when the image analyzed by the displacement calculating unit 243 is the first image (infrared image); however, it is not limited to this.

The image to be analyzed may be an image based on one or more second images (fluorescent images). Here, the "image based on one or more second images" refers to a single second image when there is one, and refers to an image obtained by superposing two or more when there are two or more.

For example, the static fluorescence image already superposed at S53 of Embodiment 3 may be used as the superposed second image. In this case, the displacement calculating unit 243 analyzes the superposed static fluorescence image and specifies the subregion corresponding to the distinctive area within this static fluorescence image. Moreover, the region extracting unit 243a extracts the specified subregion as "the image of the subregion" from among the multiple infrared images that has already been photographed (infrared images generated at S49). Then, the displacement calculating unit 243 compares the subregions within the frames of the multiple infrared images, and calculates the displacements thereof. By means of superposing the fluorescent images again using the displacements, a static fluorescence image may be obtained that is more suitable for observation of the subregion than the already superposed static fluorescence image.

Alternatively, photographed images such as color fundus images photographed using a fundus camera and past diagnosis outcomes such as schema of a fundus, which are stored in the storage unit 220, may be used as the subject to be analyzed.

As an example of when the past diagnosis outcomes are used, the displacement calculating unit 243 searches an arbitrary keyword (for example, a site such as "papilla," "macula," etc. or disease name such as "glaucoma," etc.) from texts, etc. in the past diagnosis outcomes. Then, the displacement calculating unit 243 reads the general luminance distribution of the area corresponding to the keyword from the storage unit 220. Subsequently, the displacement calculating unit 243 carries out a process of specifying the image of the coordinate values with the luminance distribution corresponding to the general luminance distribution in the first image as the image of the subregion. Further, it is also possible to use the characteristics (brightness, shape, etc.) of the area in the luminance distribution of the image instead of the general luminance distribution. Here, the "keyword" mentioned above corresponds to "the partial region" in the past diagnosis outcomes.

Embodiment 4

Figure 9:
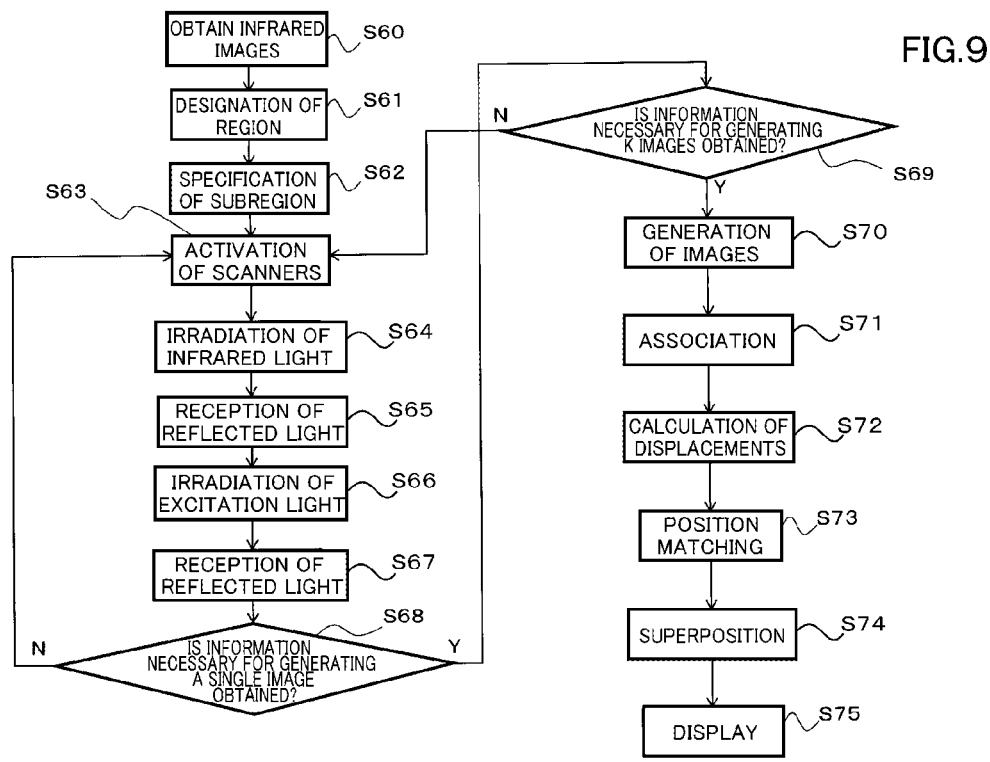
FIG. 9 is a flow chart illustrating an operation of a scanning laser ophthalmoscope according to Embodiment 4.

Next, the scanning laser ophthalmoscope 1 according to Embodiment 4 is described with reference to FIG. 9. It should be noted that the device configuration is the same as Embodiment 3, so descriptions thereof are omitted.

In Embodiment 3, a configuration is described in which the displacement calculating unit 243 automatically analyzes the first image; however, it is not limited to this. In the present embodiment, a configuration of manually specifying a partial region in the first image is described.

[Operation of Embodiment 4]

The operations of the scanning laser ophthalmoscope 1 according to Embodiment 4 are described with reference to FIG. 9. It should be noted that static images are displayed in the present embodiment.

In the present embodiment, a series of operations for superposing and displaying a fluorescent image are described. It is assumed that a fluorescent agent such as fluorescein is intravenously injected into the patient in advance. It should be noted that the following operation may also be applied for observing autofluorescence.

The scanning laser ophthalmoscope 1 scans the fundus Ef with multiple scanning points $P_{ij}$ (i=1 to M, j=1 to N), forming a single image based on the reflected lights obtained from the respective scanning points $P_{ij}$.

First, the first scanner 105 and the second scanner 107 scan the fundus Ef ($P_{ij}$ (i=1 to M, j=1 to N)) with the infrared light from the laser light source 101a based on instructions from the operation unit 232, etc. to obtain infrared images (S60). The infrared images are generated by the image generating unit 241. In the present embodiment, the images obtained at S60 are displayed on the display unit 231.

Next, the tester observes the infrared images displayed on the display unit 231, and specify the partial region in which focused observation is desired in the infrared images using the operation unit 232 (S61).

Based on the specifications in S61, the displacement calculating unit 243 specifies the subregion corresponding to the partial region in the infrared images obtained at S60 (S62). Specifically, the displacement calculating unit 243 obtains the coordinate values of the distinctive area $\epsilon$ (for example, papilla and macula; alternatively, blood vessels and bifurcation points thereof; further, lesion sites) corresponding to the designated region within the infrared images, and carries out a process of specifying the range of these coordinate values as the subregion.

Subsequently, the control unit 210 activates the first scanner 105 and the second scanner 107 based on instructions to commence photographing from the operation unit 232, etc. and matches the position of the infrared light from the laser light source 101a and the excitation light from the laser light source 101b to a certain point ($P_{11}$) of the fundus Ef to be irradiated (S63).

Next, the infrared light from the laser light source 101a is irradiated onto $P_{11}$ using the first scanner 105 and the second scanner 107 (S64). Then, the photodetector 2a receives the fundus reflected light of the infrared light irradiated at S64 (S65).

In the same manner, the excitation light from the laser light source 101b is irradiated onto the same position ($P_{11}$) as the position of the fundus Ef irradiated with the infrared light at S64 using the first scanner 105 and the second scanner 107 (S66). Then, the photodetector 3a receives the fundus reflected light (agent fluorescence) generated by the excitation light irradiated at S66 (S67).

The operations S64 to S67 are repeated until the information necessary for generating a single image (one each of an infrared image and a fluorescent image) is obtained (from $P_{11}$ to $P_{MN}$. S68: Y)). In the event that the information necessary for generating a single image has not been obtained (S68: N), the first scanner 105 and the second scanner 107 are activated (scans) by the control unit 210 (S63), and the same operations S64 to S67 are carried out at positions different from the previously photographed position.

Operations S64 to S67 are routinely repeated in this manner while sequentially changing the scanning points $P_{ij}$, and once photographing of a certain photographing range ($P_{11}$ to $P_{MN}$) a predetermined number of times (for example, 40 times) is completed (Y at S69), image processing is carried out by the image processing unit 240. Meanwhile, in the event that photographing the predetermined number of times has not been completed (N at S69), the first scanner 105 and the second scanner 107 are activated by the control unit 210 (S63), and photographing is continued upon returning to $P_{11}$ (S64 to S67).

In the case of "Y" at S69, the image generating unit 241 generates multiple infrared images based on the fundus reflected light received by the photodetector 2a. Moreover, the image generating unit 241 generates multiple fluorescent images based on the fundus reflected light (agent fluorescence) received by the photodetector 3a (S70).

Next, the associating unit 242 associates the infrared images and the fluorescent images generated at S70 (S71). For example, the associating unit 242 associates the infrared image $G_1$ and the fluorescent image $H_1$ based on the reflected light received at substantially the same timing as a pair. The associating unit 242 carries out this association regarding all photographed images. Thereby, the first image $G_k$ and the second image $H_k$ are associated (k=1 to K; K indicates the number of images).

The displacement calculating unit 243 calculates the displacements between the multiple infrared images generated at S70 (S72). For this purpose, in the present embodiment, the region extracting unit 243a extracts the subregions of the infrared image $G_k$ and the fluorescent image $H_k$ associated at S71, respectively, based on the coordinate values of the images within the subregions specified at S62. Specifically, for example, pattern matching of the subregion specified at S62 is carried out with respect to the first image in order to specify the subregion in the first image (the coordinate values of the subregion). Next, regarding this second image associated with this first image, the image consisted of the pixel of the same coordinate values as the subregion of this first image is extracted as "the image of the subregion." Then, the displacement calculating unit 243 compares the subregion in the frame of the infrared image $G_1$ with the subregion in the frame of the infrared image $G_k$ (k≥2), and calculates the displacement thereof. This process obtains, for example, the respective displacements of infrared image $G_2$ to $G_K$ with respect to infrared image $G_1$, with this as the standard.

Next, the position matching unit 244 matches the position between the fluorescent images based on the processing result of S71 and the displacement calculated at S72 (S73). Specifically, when the displacement of the subregion in the infrared image $G_k$ (k≥2) with respect to the subregion in the infrared image $G_1$ is δ, it is assumed that the displacement of fluorescent image $H_k$ with respect to fluorescent image $H_1$ is also δ. This assumption may be said to be valid from the fact that infrared image $G_1$ and fluorescent image $H_1$ photographed almost simultaneously are associated, while the infrared image $G_k$ and the fluorescent image $H_k$ photographed almost simultaneously are associated by the associating unit 242. Thus, the position matching unit 244 matches the position of fluorescent image $H_k$ with respect to fluorescent image $H_1$ by a process of shifting it by displacement $-\beta$.

Regarding the multiple fluorescent images $H_k$ that have undergone position matching at S73, the superposing unit 245 superposes the fluorescent images $H_k$ thereof in order to form a single static image (S74). Subsequently, the fluorescent image superposed at the superposing unit 245 is displayed on the display unit 231, thereby allowing a tester to observe the fluorescent image (S75).

[Action and Effect of Embodiment 4]

According to the present embodiment, with respect to the first image displayed on the display unit 231, the partial region thereof may be specified using the operation unit 232. The displacement calculating unit 243 specifies the designated region as the subregion using the operation unit 232.

According to such an embodiment, the area the tester wishes to observe may be specified within the image, thereby allowing position matching of the image corresponding to the needs of the user to be carried out with high accuracy.

[Modified Example of Embodiment 4]

Embodiment 4 described a case when the image in which the partial region thereof is specified by the operation unit 232 is the first image (infrared image); however, it is not limited to this.

In the same manner as the modified example of Embodiment 3, the image may be, for example, an image based on one or more second images (fluorescent images) (superposed second image). Alternatively, the photographed images such as the color fundus image, etc. photographed using the fundus camera, etc. and past diagnosis outcomes of the schema, etc.

of the fundus, which are stored in the storage unit 220 may be used as the subject to be designated.

The static fluorescence image already superposed at S73 may be used as the superposed second image. In this case, the partial region in which focused observation is desired within the static fluorescence image is specified by the operation unit 232. The displacement calculating unit 243 specifies the subregion corresponding to this partial region. Moreover, the region extracting unit 243a extracts the specified subregions from the multiple already photographed infrared images (infrared images generated at S70) as "the image of the subregion." Then, the displacement calculating unit 243 compares the subregions within the frames of the multiple infrared images and calculates the displacements thereof. These displacements are used to superpose the fluorescent images again; thereby, a static fluorescence image may be obtained that is more suitable for observation of the subregion than the already superposed static fluorescence image.

[Modified Example 1 of Embodiment 3 and Embodiment 4]

In Embodiment 3 and Embodiment 4, configurations are mentioned whereby the infrared image and fluorescent image are obtained at the same timing at the subregion as well as the other regions; however, it is not limited to this.

Depending on the tester, there are cases in which only the subregion corresponding to the area desired to be observed is desired to be looked at. In this case, the first laser light and second laser light may scan only the subregion specified by the displacement calculating unit 243.

In this case, first, the information necessary for generating a single infrared image is obtained using the scanning laser ophthalmoscope 1 (for example, operations S42 to S47 in Embodiment 3). The image generating unit 241 generates a single infrared image based on this information. Then, pattern matching of the subregion specified by the displacement calculating unit 243 with respect to the infrared image thereof is carried out, and thereby the displacement calculating unit 243 is rendered capable of obtaining the coordinate values of the subregion of the infrared image corresponding to this subregion.

By means of the control unit 210 controlling the scanner such that the first laser light and second laser light scans only within the range of the coordinate values (within the subregion) based on these coordinate values, the infrared image $g_k$ (k=1 to K) consisting only of the subregion and the fluorescent image $h_k$ (k=1 to K) consisting only of the parallelly photographed subregion may be obtained.

Then, the associating unit 242 associates the first image and second image based on the first laser light and second laser light parallelly scanned by the scanning unit. Moreover, the displacement calculating unit 243 calculates the displacements between images regarding the multiple infrared images $g_k$. Moreover, the position matching unit 244 matches the positions between the multiple fluorescent images $h_k$ based on the processing result from the associating unit 242 and the displacements calculated by the displacement calculating unit 243. Moreover, the superposing unit 245 superposes the multiple fluorescent images $h_k$ that have undergone position matching. Moreover, the display unit 231 displays the image obtained by superposing the multiple fluorescent images $h_k$.

Moreover, the subject to be controlled by the control unit 210 is not limited to the activation timing of the scanning unit.

For example, control is possible in which the control unit 210 carries out the detection of activation timings of the scanning unit and emission of the light source only when the scanning region of the scanning unit is within the subregion (controlling the operation of the light source).

Alternatively, the control unit 210 is capable of carrying out control of detecting the activation timing of the scanning unit and receiving light by the light receiving unit only when the scanning region of the scanner is within the subregion (controlling the operation of the light receiving unit).

Further, the control unit 210 may carry out at least two or more controls from among the timing of laser scanning, the timing of emitting the light source, and the timing of receiving light by the light receiving unit based on the instructions input from the operation unit 232.

In this manner, in the modified examples, it is possible to obtain images consisting only of the subregions and to superpose these images. Accordingly, the fluorescent images of the subregions may be accurately superpositioned. Further, acceleration of the process may be strived for compared to when scanning the entire observation region (a region at which the infrared images and fluorescent images are acquired) at the same timing.

[Modified Example 2 of Embodiment 3 and Embodiment 4]

Depending on the tester, there are cases in which clear images are desired regarding the subregion and other regions may be displayed with low resolution.

In this case, the control unit 210 may control to switch over the activation timing of the scanning unit in the subregion and the activation timing of the scanning unit in other fundus regions based on the instructions input from the operation unit 232 (controlling the operation of the scanning unit). Specifically, the control unit 210 activates the first scanner 105 and the second scanner 107 so as to densely carry out laser scanning in the subregion along with activating the first scanner 105 and the second scanner 107 so as to roughly carry out laser scanning in the other fundus regions. Here, "dense" refers to when the distance between the adjacent scanning points is small. Meanwhile, "rough" refers to when the distance between the adjacent scanning points is wide (rough) compared to "dense".

In this case, the image generating unit 241 generates the first image (infrared image) from the dense image information based on the reflected light of the first laser light in the subregion and the rough image information based on the reflected light of the first laser light in the other fundus regions. Moreover, the image generating unit 241 generates the second image (fluorescent image) from the dense image information (with high information content) based on the reflected light of the second laser light in the subregion and the rough image information (with low information content) based on the reflected light of the second laser light in the other fundus regions.

Then, the associating unit 242 associates the first image and second image based on the first laser light and second laser light parallelly scanned by the scanning unit. Moreover, the displacement calculating unit 243 calculates the displacements between images regarding the multiple first images. Moreover, the position matching unit 244 matches the positions between the multiple second images based on the processing result from the associating unit 242 and the displacements calculated by the displacement calculating unit 243. Moreover, the superposing unit 245 superposes the multiple second images that have undergone position matching. Moreover, the display unit 231 displays the image obtained by superposing the multiple second images.

Moreover, the subject to be controlled by the control unit 210 is not limited to the activation timing of the scanning unit.

For example, the control unit 210 is capable of carrying out control of switching over the timing of emitting the light source onto the subregion and the timing of emitting the light source onto the other fundus regions (controlling the operation of the light source). Specifically, the control unit 210 activates the laser light source 101a (laser light source 101b) such that the emission timings (the emission timing of the pulsed light) of the laser light source 101a (laser light source 101b) with respect to the other fundus regions are frequently switched over regarding the subregion.

Alternatively, the control unit 210 is capable of carrying out control of switching over the timing at which the light receiving unit receives light onto the subregion and the timing at which the light receiving unit receives light onto the other fundus regions (controlling the operation of the light receiving unit). Specifically, the control unit 210 activates the photodetector 2a (photodetector 3a) such that the timing at which light is received by the photodetector 2a (photodetector 3a) is switched over more frequently regarding the subregion compared to the other fundus regions.

Further, the control unit 210 is also capable of carrying out control of switching over at least two from among the timing of laser scanning, the timing of emitting the light source, and the timing at which light is received by the light receiving unit based on the instructions input from the operation unit 232.

In this manner, in the modified example, the image of the subregion and the images of the other fundus regions are obtained at different timings (rough and dense), and these images may be superposed. Thus, the fluorescent images of the subregions may be accurately superpositioned. Further, compared to when scanning the entire observation region (the region at which the infrared image and fluorescent image are obtained) at the same timing, acceleration of the process may be strived for.

[Common Modified Examples Regarding Embodiments 1 to Embodiment 4]

In the embodiments mentioned above, the infrared images generated by the image generating unit 241 are only used for matching the position of the fluorescent images; however, it is not limited to this. For example, the misregistration between the infrared images may be corrected (position-matching) by the position matching unit 244 based on the displacements calculated by the displacement calculating unit 243; thereby, the infrared images may be displayed onto the display unit 231 in parallel with the fluorescent images or by the infrared images alone. Further, the infrared images are often displayed by superposing approximately 10 images thereof.

The optical system is not limited to the configurations of the present embodiments as long as it is a configuration capable of alternately irradiating the first laser light and the second laser light, in addition to alternately receiving the fundus reflected lights from these laser lights. For example, a configuration is possible of arranging a polarization beam splitter instead of the half-mirror 104 and installing half-mirrors instead of the polarization beam splitters 103a and 103b.

The cases of displaying the static images are described in the embodiments mentioned above, but it is also possible to display dynamic images. Specifically, the associating process is carried out every time each of the first image $G_k$ and the second image $G_k$ are photographed. Moreover, every time the first image $G_k$ is photographed, the displacement calculating process may be carried out between this and the first image $G_1$. Moreover, the position matching process of the second image $G_k$ with respect to the second image $G_1$ may be carried out based on this displacement. Subsequently, the images that have undergone the position matching process are successively displayed on the display unit 231, allowing the tester to observe the second image $G_k$ as the dynamic image.

In the embodiments mentioned above, descriptions are provided under the assumption that the light emitted from the laser light source 101a and the laser light source 101b is pulsed light; however, realization is also possible with continuous light.

EXPLANATION OF THE SYMBOLS

1 Scanning laser ophthalmoscope
2, 3 Photographing device
2a, 3a Photodetector
101a, 101b Laser light source
105 First scanner
107 Second scanner
210 Control unit
220 Storage unit
230 UI
231 Display unit
232 Operation unit
240 Image processing unit
241 Image generating unit
242 Associating unit
243 Displacement calculating unit
244 Position matching unit
245 Superposing unit

What is claimed is:

1. A scanning light ophthalmic imaging apparatus, comprising:
    a light source unit that emits first-light and second light with a different wavelength from that of the first light;
    a scanning unit that two-dimensionally scans the first light and second-light, respectively, at-an eye;
    a light receiving unit that respectively receives reflected light of the first-light and the second light irradiated onto the eye by the scanning unit;
    an image generating unit that generates a first image based on the reflected light of the first light and a second image based on the reflected light of the second light;
    an associating unit that associates the first image and the second image based on the first light and the second light parallelly scanned by the scanning unit;
    a displacement calculating unit that calculates displacements between a plurality of first images;
    a position matching unit that matches the positions of a plurality of second images based on the processing result from the associating unit and the displacements;
    a superposing unit that superposes the second images that have undergone the position matching; and
    a display unit that displays an image obtained by superposing the-second images.

2. The scanning light ophthalmic imaging apparatus according to claim 1, wherein
    the first light is an infrared light, while the second light is an excitation light, and
    the second image is a fluorescent image based on a light receiving result from the light receiving unit of a fluorescence generated by the excitation light.

3. The scanning light ophthalmic imaging apparatus according to claim 1, comprising:
    an evaluating unit that evaluates the luminance of the second image; and
    a managing unit that switches whether or not processing is performed by at least any from among the associating unit, the displacement calculating unit, and the position matching unit based on the evaluation result from the evaluating unit.

4. The scanning light ophthalmic imaging apparatus according to claim 1, wherein the displacement calculating unit calculates, as the displacements, displacements between images in a subregion regarding images within the subregion of the first image.

5. The scanning light ophthalmic imaging apparatus according to claim 1, wherein
first images extracted by the region extracting unit, and
the position matching unit matches the positions of images within the subregions of the second images extracted by the region extracting unit based on the displacements between the images within the subregions calculated by the displacement calculating unit.

6. The scanning light ophthalmic imaging apparatus according to claim 4, wherein;
the displacement calculating unit analyzes the first image to specify a partial region thereof, and specifies the region within the first image corresponding to the partial region as the subregion.

7. The scanning light ophthalmic imaging apparatus according to claim 5, wherein;
the displacement calculating unit analyzes the first image to specify a partial region thereof, and specifies the region within the first image corresponding to the partial region as the subregion.

8. The scanning light ophthalmic imaging apparatus according to claim 4, comprising an operation unit for designating the partial region of the first image displayed on the display unit, wherein,
the displacement calculating unit specifies the region designated using the operation unit as the subregion.

9. The scanning light ophthalmic imaging apparatus according to claim 5, comprising an operation unit for designating the partial region of the first image displayed on the display unit, wherein,
the displacement calculating unit specifies the region designated using the operation unit as the subregion.

10. The scanning light ophthalmic imaging apparatus according to claim 4, wherein;
the displacement calculating unit analyzes an image based on one or more second images to specify a partial region thereof, and specifies the region within the first image corresponding to the partial region as the subregion.

11. The scanning light ophthalmic imaging apparatus according to claim 5, wherein;
the displacement calculating unit analyzes an image based on one or more second images to specify a partial region thereof, and specifies the region within the first image corresponding to the partial region as the subregion.

12. The scanning light ophthalmic imaging apparatus according to claim 4, comprising an operation unit for designating a partial region of an image based on one or more second images displayed on the display unit, wherein;
the displacement calculating unit specifies the region within the first image corresponding to the region designated using the operation unit as the subregion.

13. The scanning light ophthalmic imaging apparatus according to claim 5, comprising an operation unit for designating a partial region of an image based on one or more second images displayed on the display unit, wherein;
the displacement calculating unit specifies the region within the first image corresponding to the region designated using the operation unit as the subregion.

14. The scanning light ophthalmic imaging apparatus according to claim 4, comprising a storage unit to store previous images or previous diagnosis outcomes, wherein;
the displacement calculating unit analyzes the previous images or past diagnosis outcomes to specify the subregion.

15. The scanning light ophthalmic imaging apparatus according to claim 5, comprising a storage unit to store previous images or previous diagnosis outcomes, wherein;
the displacement calculating unit analyzes the previous images or past diagnosis outcomes to specify the subregion.

16. The scanning light ophthalmic imaging apparatus according to claim 14, comprising an operation unit for designating a partial region of the previous images or the past diagnosis outcomes displayed on the display unit, wherein;
the displacement calculating unit specifies the region designated using the operation unit as the subregion.

17. The scanning light ophthalmic imaging apparatus according to claim 15, comprising an operation unit for designating a partial region of the previous images or the past diagnosis outcomes displayed on the display unit, wherein;
the displacement calculating unit specifies the region designated using the operation unit as the subregion.

18. The scanning light ophthalmic imaging apparatus according to claim 4, comprising a control unit that controls the scanning unit such that the first light and the second light are only scanned within the subregion.

19. The scanning light ophthalmic imaging apparatus according to claim 5, comprising a control unit that controls the scanning unit such that the first light and the second light are only scanned within the subregion.

20. The scanning light ophthalmic imaging apparatus according to claim 4, comprising a control unit that controls the scanning unit such that the first light and the second light are densely scanned in the subregion while these are roughly scanned in other regions.

21. The scanning light ophthalmic imaging apparatus according to claim 5, comprising a control unit that controls the scanning unit such that the first light and the second light are densely scanned in the subregion while these are roughly scanned in other regions.

22. The scanning light ophthalmic imaging apparatus according to claim 1, wherein the light source unit alternately emits the first light and the second light.

* * * * *